United States Patent
Wang et al.

(10) Patent No.: US 12,386,003 B2
(45) Date of Patent: Aug. 12, 2025

(54) MAGNETIC RESONANCE IMAGING METHOD AND APPARATUS BASED ON TWO-DIMENSIONAL FAST SPIN ECHO

(71) Applicant: Siemens Healthcare GmbH, Erlangen (DE)

(72) Inventors: Yu Yu Wang, Shenzhen (CN); De He Weng, Shenzhen (CN); Kun Zhou, Shenzhen (CN); Le Zhang, Shenzhen (CN)

(73) Assignee: Siemens Healthineers AG, Erlangen (DE)

( * ) Notice: Subject to any disclaimer, the term of this patent is extended or adjusted under 35 U.S.C. 154(b) by 1370 days.

Patent file contains an affidavit/declaration under 37 CFR 1.130(b).

(21) Appl. No.: 16/729,799

(22) Filed: Dec. 30, 2019

(65) Prior Publication Data

US 2020/0205693 A1     Jul. 2, 2020

(30) Foreign Application Priority Data

Dec. 28, 2018    (CN) .......................... 201811618720.9

(51) Int. Cl.
*G01R 33/561*     (2006.01)
*G01R 33/48*      (2006.01)
(Continued)

(52) U.S. Cl.
CPC ......... *G01R 33/561* (2013.01); *G01R 33/483* (2013.01); *G01R 33/543* (2013.01);
(Continued)

(58) Field of Classification Search
CPC .... A61B 5/055; G01R 33/483; G01R 33/586; G01R 33/50; G01R 33/56; G01R 33/5615;
(Continued)

(56) References Cited

U.S. PATENT DOCUMENTS

2011/0274331 A1   11/2011   Weng
2013/0342202 A1   12/2013   Mugler, III et al.
(Continued)

FOREIGN PATENT DOCUMENTS

CN    102232831 A    11/2011
CN    103118593 A    5/2013
(Continued)

OTHER PUBLICATIONS

Wang, Yuyu, et al. "Fast Blade with variable flip angle." ISMRM. Jun. 2018. (Year: 2018).*
(Continued)

*Primary Examiner* — Rishi R Patel
(74) *Attorney, Agent, or Firm* — Banner & Witcoff Ltd.

(57) ABSTRACT

In a magnetic resonance imaging method, a first adjustment parameter is determined for presetting an initial contrast of a magnetic resonance image; a second adjustment parameter is determined for obtaining an optimized contrast of the magnetic resonance image and a specified data acquisition time of a blade artifact correction sequence; an optimized echo signal evolution curve is determined according to the first adjustment parameter and the second adjustment parameter; an actual variable flip angle train is calculated according to the optimized echo signal evolution curve; and the actual variable flip angle train is applied to a two-dimensional fast spin echo sequence, and the blade artifact correction sequence corresponding to the second adjustment parameter is used to acquire magnetic resonance signals and enable the magnetic resonance image to satisfy the optimized contrast.

19 Claims, 6 Drawing Sheets

(51) Int. Cl.
  *G01R 33/483* (2006.01)
  *G01R 33/50* (2006.01)
  *G01R 33/54* (2006.01)
  *G01R 33/56* (2006.01)
  *G01R 33/58* (2006.01)

(52) U.S. Cl.
  CPC ........ *G01R 33/586* (2013.01); *G01R 33/4824* (2013.01); *G01R 33/50* (2013.01); *G01R 33/56* (2013.01); *G01R 33/5615* (2013.01); *G01R 33/5617* (2013.01); *G01R 33/58* (2013.01)

(58) Field of Classification Search
  CPC .. G01R 33/58; G01R 33/5602; G01R 33/543; G01R 33/4824; G01R 33/5617; G01R 33/54; G01R 33/4826; G01R 33/482; G01R 33/561
  See application file for complete search history.

(56) References Cited

U.S. PATENT DOCUMENTS

| | | | |
|---|---|---|---|
| 2014/0003694 A1 | 1/2014 | Weng | |
| 2014/0009157 A1 | 1/2014 | Umeda | |
| 2018/0092569 A1* | 4/2018 | Li | G01R 33/022 |
| 2019/0064295 A1* | 2/2019 | Wang | G01R 33/543 |

FOREIGN PATENT DOCUMENTS

| | | | | |
|---|---|---|---|---|
| CN | 103505210 A | 1/2014 | | |
| CN | 108318843 A | 7/2018 | | |
| CN | 108983133 A | 12/2018 | | |
| JP | 2016086991 A | 5/2016 | | |
| WO | WO-2018187040 A1 * | 10/2018 | ......... | G01R 33/5602 |
| WO | 2020019851 A1 | 1/2020 | | |

OTHER PUBLICATIONS

"Propeller/Blade" by Questions and Answers in MRI, <https://mriquestions.com/propellerblade.html> (Year: 2024).*

Pipe et al., "Turboprop: Improved Propeller Imaging," Magnetic Resonance in Medicine, vol. 55, No. 2, pp. 380-385 (2006).

Liang, Hanhuan et al. "The Value of BIADE and SSTSE T2WI in the Brain" China Modern Doctor, vol. 47, No. 23, pp. 105-106, 2009 (with English-language Abstract).

Weng, De-he, "Technical detail of Blade" Chinese Journal Magnetic resonance imaging, vol. 1, No. 5, pp. 376-379, 2010 (with English-language Abstract).

Hu Jun, "Analysis of the advantages and limitations of propeller technology in the application of head MRI scanning" Medical Journal of Chinese People's Health, vol. 23, No. 6, pp. 771-772, Mar. 2011 (with English-language translation and Abstract).

Chinese Action dated Nov. 29, 2021, Application No. 201811618720.9.

* cited by examiner

MAGNETIC RESONANCE IMAGING METHOD AND APPARATUS BASED ON TWO-DIMENSIONAL FAST SPIN ECHO

CROSS REFERENCE TO RELATED APPLICATIONS

This patent application claims priority to Chinese Patent Application No. 201811618720.9, filed Dec. 28, 2018, which is incorporated herein by reference in its entirety.

BACKGROUND

Field

The present disclosure relates to magnetic resonance imaging, including a magnetic resonance imaging method and apparatus based on two-dimensional fast spin echo.

Related Art

Magnetic resonance imaging (MRI) is a technique using magnetic resonance phenomena for imaging. The principle of magnetic resonance phenomena mainly involves nuclei containing an odd number of proton(s), for example, hydrogen nuclei widely existing in a human body, the protons thereof are in a spin motion, like small magnets, and the small magnets have irregular axes of spin. If an external magnetic field is applied, the small magnets will be rearranged according to magnetic force lines of the external magnetic field, and are specifically arranged in two directions, i.e. directions parallel to and anti-parallel to the magnetic force lines of the external magnetic field. The direction parallel to the magnetic force lines of the external magnetic field mentioned above is referred to as a positive longitudinal axis, and the direction anti-parallel to the magnetic force lines of the external magnetic field mentioned above is referred to as a negative longitudinal axis. The nuclei only have a longitudinal magnetization component that has both direction and amplitude. Nuclei in the external magnetic field are excited by radio frequency (RF) pulses at a specific frequency such that the axes of spin of the nuclei deviate from the positive longitudinal axis or the negative longitudinal axis so as to produce resonance, which is the magnetic resonance phenomenon. After the axes of spin of the excited nuclei mentioned above deviate from the positive longitudinal axis or the negative longitudinal axis, the nuclei have a transverse magnetization component.

After stopping transmitting radio frequency pulses, the excited nuclei transmit echo signals gradually release the absorbed energy in the form of electromagnetic waves, and both the phase and energy level thereof are restored to the state before being excited, and the echo signals transmitted by the nuclei are subjected to further processing such as space encoding such that the image can be reconstructed. The above process of the excited nuclei being restored to the state before being excited is referred to as a relaxation process, and the time required to restore to an equilibrium state is referred to as a relaxation time.

MRI systems are non-invasive, have a higher tissue contrast than computed tomography (CT), and do not produce artifacts due to bone tissue. Furthermore, the MRI systems can capture various cross sections in desired directions without changing the position of the scanned object.

The k-space is a data space of each cross section, and by performing Fourier transform on the k-space, a desired image can be obtained. If the magnitudes of a phase encoding gradient and a frequency encoding gradient are gradually changed after an RF pulse sequence is applied, raw data having various position information can be obtained. The raw data has position information and tissue contrast information, and the k-space represents a group of raw data that can form one image.

BRIEF DESCRIPTION OF THE DRAWINGS/FIGURES

The accompanying drawings, which are incorporated herein and form a part of the specification, illustrate the embodiments of the present disclosure and, together with the description, further serve to explain the principles of the embodiments and to enable a person skilled in the pertinent art to make and use the embodiments.

Figure 1:
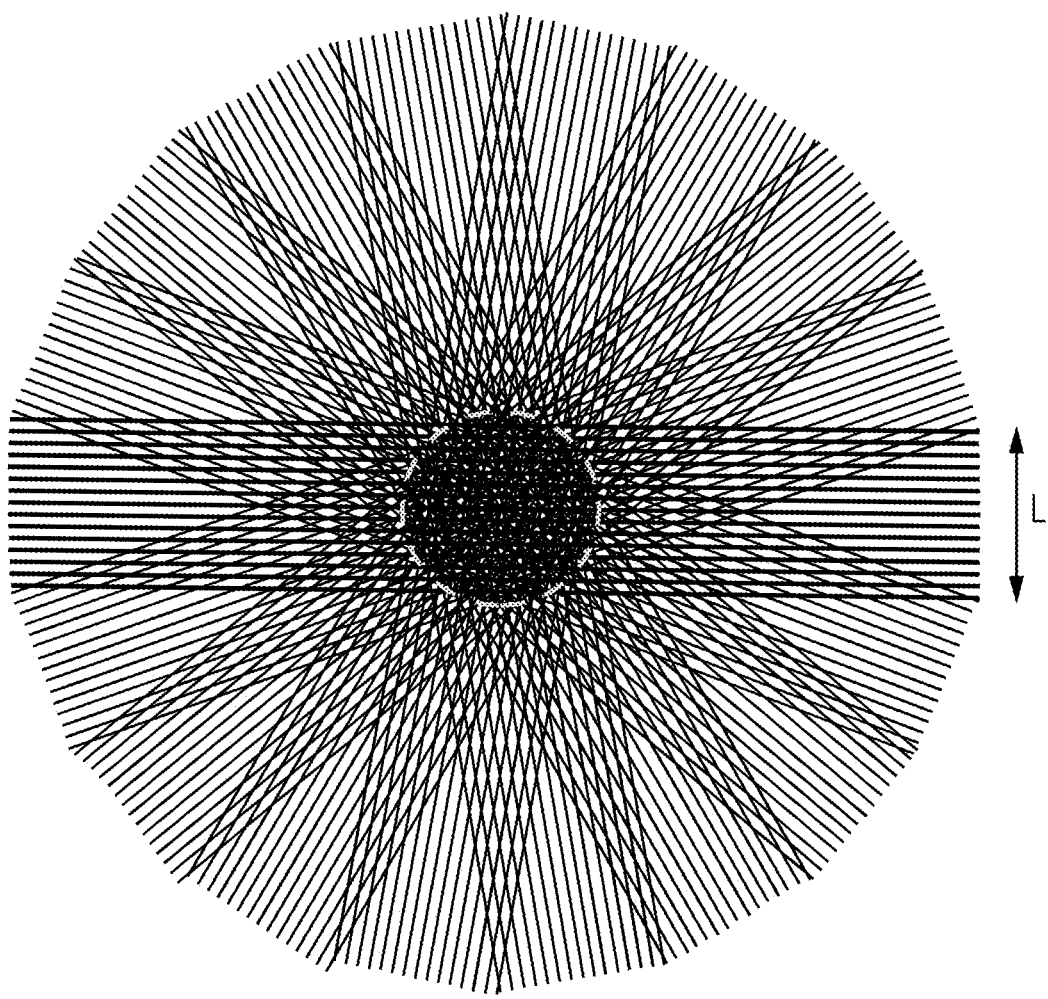
FIG. 1 is a schematic diagram of one trajectory of using a TSE BLADE sequence to acquire k-space data according to an exemplary embodiment of the present disclosure.

The exemplary embodiments of the present disclosure will be described with reference to the accompanying drawings. Elements, features and components that are identical, functionally identical and have the same effect are—insofar as is not stated otherwise—respectively provided with the same reference character.

The drawings are to be regarded as being schematic representations, and elements illustrated in the drawings are not necessarily shown to scale. Rather, the various elements are represented such that their function and general purpose becomes apparent to a person skilled in the art. Any connection or coupling between functional blocks, devices, components of physical or functional units shown in the drawings and described hereinafter may be implemented by an indirect connection or coupling. A coupling between components may be established over a wired or wireless connection. Functional blocks may be implemented in hardware, software, firmware, or a combination thereof.

DETAILED DESCRIPTION

In the following description, numerous specific details are set forth in order to provide a thorough understanding of the embodiments of the present disclosure. However, it will be apparent to those skilled in the art that the embodiments, including structures, systems, and methods, may be practiced without these specific details. The description and representation herein are the common means used by those experienced or skilled in the art to most effectively convey the substance of their work to others skilled in the art. In other instances, well-known methods, procedures, components, and circuitry have not been described in detail to avoid unnecessarily obscuring embodiments of the disclosure.

FIG. 1 is a schematic diagram of one trajectory of using a two-dimensional fast spin echo (TSE) blade artifact correction sequence (BLADE) to acquire k-space data according to an exemplary embodiment of the present disclosure. As shown in FIG. 1, one blade is acquired in one repetition time (TR), and the next blade is acquired after rotation by a certain angle (which is 20° in FIG. 1). In FIG. 1, a case where a blade width is L and an echo train length corresponding to the blade width L is 15 is taken as an example. Each TR represents one time period from one 90° pulse to the next 90° pulse in a pulse sequence. When blade scanning is performed, the relationship among the basic resolution m of an image, the number N of blades, and the blade width L satisfies the following formula (1), and the relationship among the acquisition time $T_{acq}$, the number N of blades, and the repetition time TR satisfies the following formula (2):

$$N*L = \pi*m/2 \qquad (1)$$

$$T_{acq} = N*TR \qquad (2)$$

Since oversampling occurs in the central portion of k-space, blade scanning is a time-consuming data acquisition method. For some patients who do not cooperate or when performing brain scanning, due to the presence of respiratory motion, some motion artifacts still cannot be corrected using the BLADE method. These motion artifacts sometimes even lead to an improper diagnosis due to blurred pathology. Low blade scanning efficiency hinders more diagnostic applications of blades. Therefore, it is necessary to accelerate the movement speed of the blades to alleviate the motion artifacts. It can be seen from the formulas (1) and (2) that while maintaining the basic resolution m, the number N of blades can be reduced by increasing the blade width L so as to then reduce the acquisition time $T_{acq}$. That is, increasing of the blade width L is one of the techniques of improving the blade scanning efficiency. However, the wider the blade is, the longer the echo train length is, and the more the transverse magnetization vector relaxation time T2 is attenuated, further resulting in blurred images.

In view of this, one aspect of the embodiments of the present disclosure proposes a magnetic resonance imaging method based on two-dimensional fast spin echo, and another aspect thereof proposes a magnetic resonance imaging apparatus based on two-dimensional fast spin echo, so as to ensure the imaging quality of an image when an acquisition time is shortened by increasing a blade width so as to eliminate artifacts.

The embodiments of the present disclosure propose a magnetic resonance imaging method based on two-dimensional fast spin echo, which uses a blade artifact correction sequence (BLADE) to performs data acquisition of magnetic resonance signals, the method comprising: determining a first adjustment parameter for presetting an initial contrast of a magnetic resonance image; determining a second adjustment parameter for obtaining an optimized contrast of the magnetic resonance image and a specified data acquisition time of a blade artifact correction sequence; determining an optimized echo signal evolution curve according to the first adjustment parameter and the second adjustment parameter; obtaining an actual variable flip angle train by means of calculation according to the optimized echo signal evolution curve; and applying the actual variable flip angle to a two-dimensional fast spin echo sequence, and using a blade artifact correction sequence corresponding to the second adjustment parameter to acquire magnetic resonance signals and enable the magnetic resonance image to satisfy the optimized contrast.

In an exemplary embodiment, after the step of determining a first adjustment parameter for presetting the initial contrast of the magnetic resonance image, the method further comprises: predetermining an initial echo signal evolution curve according to the first adjustment parameter; and obtaining an initial variable flip angle train by means of calculation according to the initial echo signal evolution curve.

In an exemplary embodiment, the second adjustment parameter is selected from at least one of an echo spacing and an echo train length.

In an exemplary embodiment, the step of obtaining an actual variable flip angle train by means of calculation according to the optimized echo signal evolution curve comprises: obtaining optimized variable flip angles by means of reckoning according to the optimized echo signal evolution curve; obtaining a calculated echo signal evolution curve by means of calculation according to the optimized variable flip angles; and comparing the calculated echo signal evolution curve with the optimized echo signal evolution curve and using, when the difference therebetween satisfies a specified requirement, the optimized variable flip angles as the actual variable flip angle train.

In an exemplary embodiment, the first adjustment parameter is one of the following preset three variable flip angle modes: longitudinal magnetization vector relaxation time T1-weighted, proton density PD-weighted, and transverse magnetization vector relaxation time T2-weighted.

The embodiments of the present disclosure propose a magnetic resonance imaging apparatus based on two-dimensional fast spin echo, which uses a blade artifact correction sequence to perform data acquisition of magnetic resonance signals. In an exemplary embodiment, the apparatus includes a first adjustment parameter determiner suitable for determining a first adjustment parameter for presetting an initial contrast of a magnetic resonance image; a second adjustment parameter determiner suitable for determining a second adjustment parameter for obtaining an optimized contrast of the magnetic resonance image and a specified data acquisition time of the blade artifact correction sequence; a first echo signal evolution curve determiner for determining an optimized echo signal evolution curve according to the first adjustment parameter and the second adjustment parameter; a first variable flip angle train determiner for obtaining an actual variable flip angle train by means of calculation according to the optimized echo signal evolution curve; and a magnetic resonance imaging scanner for applying the actual variable flip angle to a two-dimensional fast spin echo sequence, and using the blade artifact correction sequence corresponding to the second adjustment parameter to acquire magnetic resonance signals and enable the magnetic resonance image to satisfy the optimized contrast. In an exemplary embodiment, the MRI apparatus (including one or more of its components) includes processor circuitry that is configured to perform one or more functions and/or operations of the MRI apparatus and/or of the respective components therein.

In an exemplary embodiment, the apparatus further comprises: a second echo signal evolution curve determiner for predetermining an initial echo signal evolution curve according to the first adjustment parameter; and a second variable flip angle train determiner for obtaining an initial variable flip angle train by means of calculation according to the initial echo signal evolution curve.

In an exemplary embodiment, the second adjustment parameter determiner determines an echo spacing and/or an echo train length for obtaining the optimized contrast of the magnetic resonance image, and an echo train length for obtaining the specified data acquisition time of the blade artifact correction sequence.

In an exemplary embodiment, the first variable flip angle train determiner comprises: a first unit used for obtaining optimized variable flip angles by means of reckoning according to the predetermined echo signal evolution curve; a second unit, which obtains a calculated echo signal evolution curve by means of calculation according to the optimized variable flip angles; and a third unit, which compares the calculated echo signal evolution curve with the optimized echo signal evolution curve and uses, when the difference therebetween satisfies a specified requirement, the optimized variable flip angles as the actual variable flip angle train.

In an exemplary embodiment, the first adjustment parameter determiner determines a variable flip angle mode for presetting the initial contrast of the magnetic resonance image, the variable flip angle mode being one of the following three variable flip angle modes: longitudinal magnetization vector relaxation time T1-weighted, proton density PD-weighted, and transverse magnetization vector relaxation time T2-weighted.

It can be seen from the solutions described above that in the embodiments of the present disclosure, an optimized echo signal evolution curve is first determined; based on the echo signal evolution curve, a magnetic resonance image can satisfy a preset contrast, and the acquisition time of a BLADE sequence can satisfy a specified short-time requirement; a variable flip angle train is then obtained by means of calculation based on the optimized echo signal evolution curve; and the variable flip angle train is applied to a two-dimensional fast spin echo sequence, and a blade artifact correction sequence corresponding to the second adjustment parameter is used to acquire magnetic resonance signals. Therefore, the attenuation of T2 can be controlled by adjusting the value of a flip angle when a blade width is increased, and the imaging quality of an image can be ensured when the acquisition speed is accelerated by increasing a blade width so as to eliminate artifacts.

Furthermore, the embodiments of the present disclosure provide a simple and reliable implementation of an optimized variable flip angle.

In exemplary embodiments, to solve the above problem that accelerating the acquisition speed by means of increasing the blade width can eliminate artifacts but will cause excessive attenuation of T2 to cause blurred images, a variable flip angle is introduced for a BLADE sequence so as to control attenuation of T2 by adjusting the value of the flip angle when the blade width is increased. That is, the variable flip angle technique is a technique which increases the length of an echo train while reducing the effect of attenuation of T2.

Further, for a variable flip angle mode, an imaging parameter for adjusting a tissue contrast is set, and an image satisfying a desired tissue contrast may be implemented by adjusting the imaging parameter.

Figure 2:
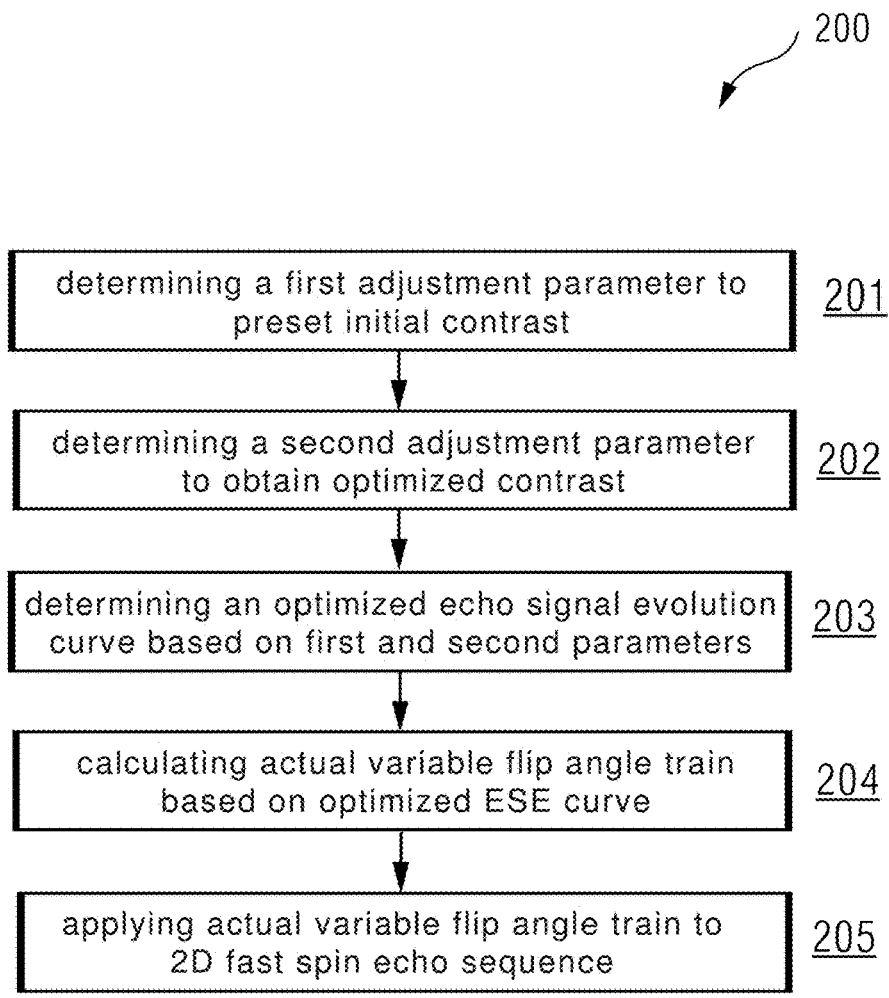
FIG. 2 is a schematic flowchart of a magnetic resonance imaging method, according to an exemplary embodiment, based on two-dimensional fast spin echo.

FIG. 2 is a schematic flowchart of a magnetic resonance imaging method 200, according to an exemplary embodiment, based on two-dimensional fast spin echo in an embodiment of the present disclosure. In an exemplary embodiment, as shown in FIG. 2, the method 200 includes the following operations 201-205.

Step 201: a first adjustment parameter for presetting an initial contrast of a magnetic resonance image is determined.

In order to implement a desired tissue contrast of a magnetic resonance image, an adjustment may be made to an existing or a newly added imaging parameter. For example, in one implementation, different variable flip angle modes may be preset, such as a longitudinal magnetization vector relaxation time (T1)-weighted variable flip angle mode, a proton density (PD)-weighted variable flip angle mode, and a transverse magnetization vector relaxation time (T2)-weighted variable flip angle mode. The T1-weighted variable flip angle mode is used such that an echo signal evolution curve conforms to the T1-weighted magnetic resonance imaging, the PD-weighted variable flip angle mode is used such that an echo signal evolution curve conforms to the PD-weighted magnetic resonance imaging, and the T2-weighted variable flip angle mode is used such that an echo signal evolution curve conforms to the T2-weighted magnetic resonance imaging.

Accordingly, the first adjustment parameter in this step may be one of the above three variable flip angle modes, for example, if it is desired to obtain the T1-weighted magnetic resonance imaging, in this step 201, it may be determined, according to a received signal corresponding to the T1-weighted variable flip angle mode that is selected by a user or a system, that the first adjustment parameter is the T1-weighted variable flip angle mode; if it is desired to obtain the T2-weighted magnetic resonance imaging, in this step 201, it may be determined, according to a received signal corresponding to the T2-weighted variable flip angle mode that is selected by a user or a system, that the first adjustment parameter is the T2-weighted variable flip angle mode; and so on.

Based on the first adjustment parameter determined in step 201, this method may further comprise: predetermining an initial echo signal evolution curve according to the first adjustment parameter; and obtaining an initial variable flip angle train by means of calculation according to the initial echo signal evolution curve.

Step 202: a second adjustment parameter for obtaining an optimized contrast of a magnetic resonance image and a specified data acquisition time of the blade artifact correction sequence is determined.

In specific implementation, after step 201 is performed, the initial contrast of the magnetic resonance image may be determined, and if the initial contrast cannot satisfy a specified requirement, the contrast can be further optimized by performing step 202, for example, by adjusting at least one of an echo spacing and an echo train length so as to achieve a contrast satisfying the specified requirement. Furthermore, a blade width may be further changed by adjusting the echo train length, and then the number of blades and a data acquisition time of a blade artifact correction sequence may be changed. The longer the echo train is, the larger the blade width is, the smaller the number of blades is, and the shorter the data acquisition time of the blade artifact correction sequence is. Accordingly, in this step, the value of at least one of the currently adjusted echo spacing and echo train length may be determined.

Step 203: an optimized echo signal evolution curve is determined according to the first adjustment parameter and the second adjustment parameter.

In this embodiment, in order to enable an echo signal evolution curve to meet the attenuation requirement of T2, corresponding parameters can be determined by steps 201 and 202, such as the variable flip angle mode, the echo spacing and the echo train length.

Figure 3A:
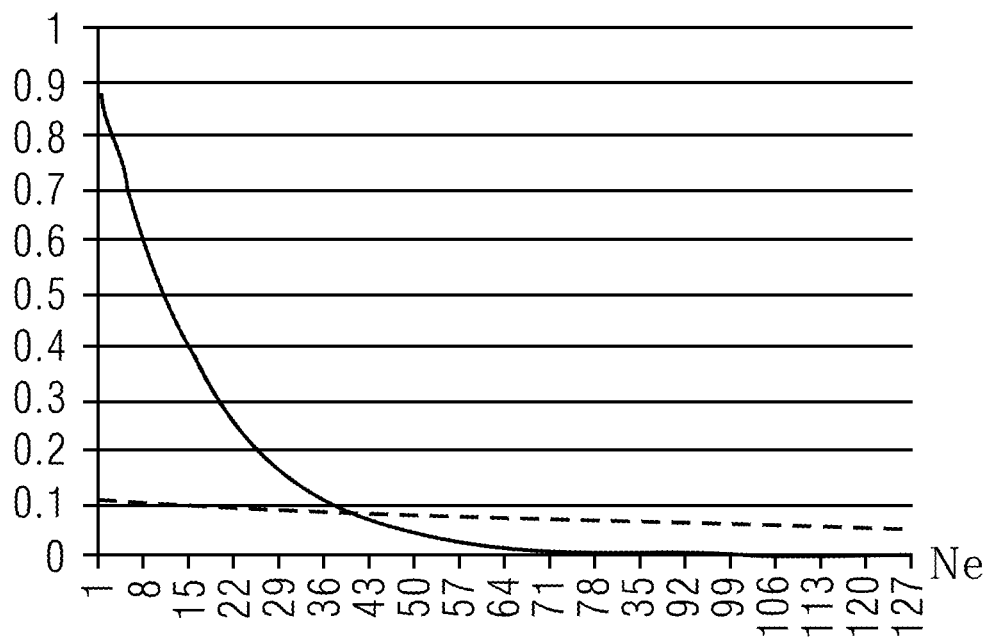
FIG. 3A is a schematic diagram of a predetermined echo signal evolution curve according to an exemplary embodiment of the present disclosure.

The optimized echo signal evolution curve is an echo signal evolution curve satisfying the specified requirement such as the attenuation requirement of T2 based on the first adjustment parameter and the second adjustment parameter. As shown by the dashed curve in FIG. 3A, FIG. 3A shows a schematic diagram of a predetermined echo signal evolution curve in one example. The horizontal coordinates in FIG. 3A are the number Ne of echoes in an echo train, wherein the maximum value 127 is corresponding to an echo train length. The vertical coordinates are normalized signal strength.

Step 204: an actual variable flip angle train is obtained by means of calculation according to the optimized echo signal evolution curve.

In one example, this step 204 may be implemented using the method as follows.

A. Optimized variable flip angles are obtained by means of reckoning according to the predetermined echo signal evolution curve.

In this step, in an exemplary embodiment, the following formula (3) for calculating a flip angle can be obtained based on an extended phase graph algorithm (EPG), and echo signal strength $F_1$ in the predetermined echo signal evolution curve is used as a known quantity based on the formula (3) and input into the formula (3), so that an optimized flip angle may be obtained by means of iteration:

$$\alpha_n = 2 * \arctan\left(\frac{-Z_1(n-1)E_1E_2 \pm \sqrt{(Z_1(n-1))^2 E_1^2 E_2^2 - (F_1(n-1)E_2^2 - I_n)(I_{n-1}E_2^2 - I_n)}}{I_{n-1}E_2^2 - I_n}\right) \quad (3)$$

$\alpha_n$ is a flip angle of the nth convergence pulse.

$E_1 = \exp(-t_{esp}/(2T_1))$ and $E_2 = \exp(-t_{esp}/(2T_2))$, which are relaxation factors.

$F_1$ (n−1) may be considered as a predetermined signal (horizontal) obtained after the (n−1)th radio frequency pulse is applied, and may be adjusted by protocol parameters (such as an echo spacing $t_{esp}$, an echo train length (which is equal to the maximum value of n), $T_1$, and $T_2$).

$Z_1(n-1)$ is longitudinal magnetization intensity obtained after the (n−1)th radio frequency pulse is applied.

The initial state of F and Z is $[F_1(0), F_{-1}(0), Z_1(0)]=[1, 0, 0]$, and is produced by a 90° excitation pulse.

$I_n$ is signal strength of the nth echo, and is equal to $E_2 F_{-1}(n)$.

Figure 3B:
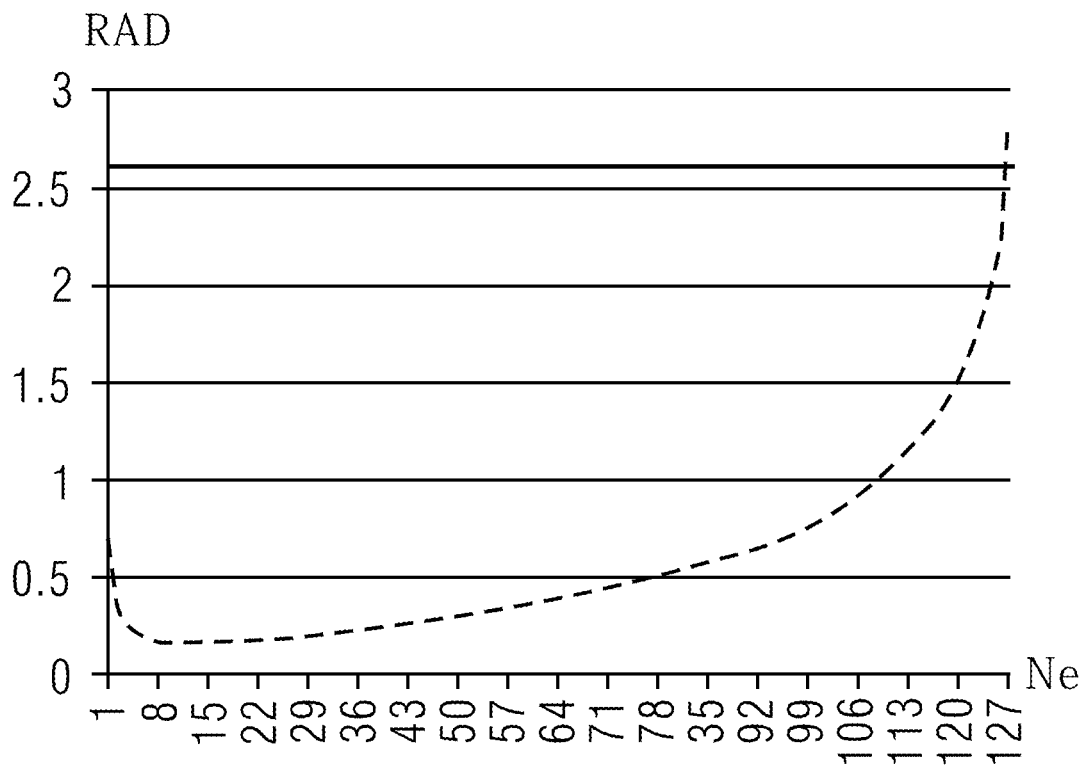
FIG. 3B is a schematic diagram of an optimized variable flip angle according to an exemplary embodiment of the present disclosure.

As shown by the dashed curve in FIG. 3B, FIG. 3B is a schematic diagram of an optimized variable flip angle obtained by means of reckoning according to the predetermined echo signal evolution curve shown in FIG. 3A in one example of the present disclosure. The horizontal coordinates in FIG. 3B are the number Ne of echoes in an echo train, and the vertical coordinates are variable flip angles in units of radians (RAD).

B. A calculated echo signal evolution curve is obtained by means of calculation according to the optimized variable flip angles.

In this step, similarly, by using the optimized flip angle α obtained in step B as a known quantity, a corresponding echo signal evolution curve I, i.e. the calculated echo signal evolution curve may be obtained by means of reckoning by the formula (3).

In practical applications, due to the presence of calculation errors, there may be some differences between the echo signal evolution curve obtained after back-stepping in step B and the optimized echo signal evolution curve obtained in step 203.

C. The calculated echo signal evolution curve is compared with the predetermined echo signal evolution curve, and when the difference therebetween satisfies a specified requirement, the optimized variable flip angles is used as the actual variable flip angle train.

The difference between the calculated echo signal evolution curve and the predetermined echo signal evolution curve needs to be as little as possible.

Step 205: the actual variable flip angle train is applied to a two-dimensional fast spin echo sequence, and a blade artifact correction sequence corresponding to the second adjustment parameter is used to acquire magnetic resonance signals and enable a magnetic resonance image to satisfy the optimized contrast.

The magnetic resonance imaging method based on two-dimensional fast spin echo in the embodiments of the present disclosure has been described in detail above, and a magnetic resonance imaging apparatus based on two-dimensional fast spin echo in the embodiments of the present disclosure is then described in detail below. For the details which are not disclosed in the apparatus embodiment of the present disclosure, reference may be made to corresponding descriptions in the method embodiment of the present disclosure.

Figure 4:
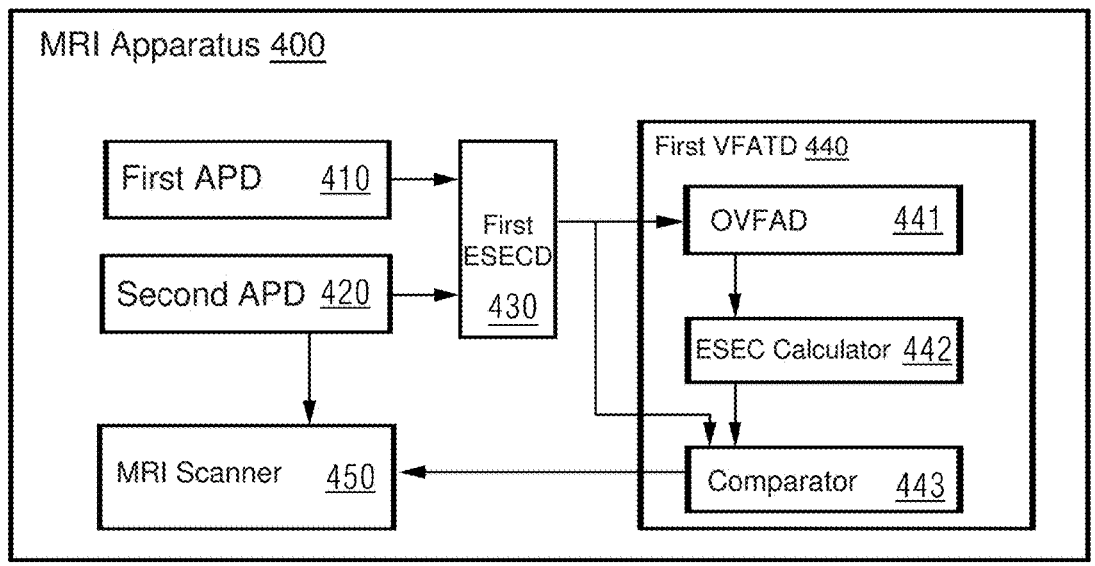
FIG. 4 is a magnetic resonance imaging apparatus, according to an exemplary embodiment of the present disclosure, based on two-dimensional fast spin echo.

FIG. 4 is a schematic structural diagram of a magnetic resonance imaging apparatus 400, according to an exemplary embodiment, based on two-dimensional fast spin echo in an embodiment of the present disclosure. The apparatus 400 in the embodiment may be used for implementing the method in the embodiment shown in FIG. 2. As shown by the solid-line portion in FIG. 4, in an exemplary embodiment, the apparatus includes: a first adjustment parameter determiner 410, a second adjustment parameter determiner 420, a first echo signal evolution curve determiner 430, a first variable flip angle train determiner 440 and a magnetic resonance imaging scanner 450. In an exemplary embodiment, components 410, 420, 430, 440, and/or 450 include processor circuitry that is configured to perform one or more respective functions and/or operations. In an exemplary embodiment, the MRI apparatus 400 includes a processor, where components 410, 420, 430, and 440 are functional blocks of the processor. In this example, the components 441, 442, and 443 are functional sub-blocks of the first variable flip angle train determiner 440. In an exemplary embodiment, the functional blocks/sub-blocks can be embodied in one or more respective processors.

In another embodiment, the MRI apparatus 400 includes circuitry, where components 410, 420, 430, and 440 are sub-circuits of the circuitry.

The first adjustment parameter determiner 410 is configured to determine a first adjustment parameter for presetting an initial contrast of a magnetic resonance image.

For example, in one implementation, a user may make an adjustment to an existing or a newly added imaging parameter according to a desired tissue contrast of a magnetic resonance image. For example, different variable flip angle modes may be preset, such as a T1-weighted variable flip angle mode, a PD-weighted variable flip angle mode and a T2-weighted variable flip angle mode. The T1-weighted variable flip angle mode is used such that an echo signal evolution curve conforms to the T1-weighted magnetic resonance imaging, the PD-weighted variable flip angle mode is used such that an echo signal evolution curve conforms to the PD-weighted magnetic resonance imaging, and the T2-weighted variable flip angle mode is used such that an echo signal evolution curve conforms to the T2-weighted magnetic resonance imaging. Accordingly, the first adjustment parameter determiner 410 may determine, according to the selection of a user or a system, that the first adjustment parameter is a variable flip angle mode with corresponding weight.

The second adjustment parameter determiner 420 is configured to determine a second adjustment parameter for obtaining an optimized contrast of a magnetic resonance image and a specified data acquisition time of the blade artifact correction sequence. For example, in one implementation, the second adjustment parameter determiner 420 may determine an echo spacing and/or an echo train length for obtaining the optimized contrast of the magnetic resonance image, and an echo train length for obtaining the specified data acquisition time of the blade artifact correction sequence.

The echo signal evolution curve determiner 430 determines an optimized echo signal evolution curve according to the first adjustment parameter and the second adjustment parameter.

The variable flip angle train determiner 440 is configured to calculate an actual variable flip angle train according to the optimized echo signal evolution curve.

The magnetic resonance imaging scanner 450 is configured to apply the actual variable flip angle to a two-dimensional fast spin echo sequence, and use a blade artifact correction sequence corresponding to the second adjustment parameter to acquire magnetic resonance signals and enable a magnetic resonance image to satisfy the optimized contrast.

In one implementation, after the first adjustment parameter determiner 410 determines the first adjustment parameter, the echo signal evolution curve determiner 430 may be further used for predetermining an initial echo signal evolution curve according to the first adjustment parameter; and accordingly, the variable flip angle train determiner 440 may be further used for obtaining an initial variable flip angle train by means of calculation according to the initial echo signal evolution curve.

In an exemplary embodiment, the variable flip angle train determiner 440 includes: a first unit 441, a second unit 442 and a third unit 443.

The first unit (e.g. optimized variable flip angles determiner) 441 is used for obtaining optimized variable flip angles by means of reckoning according to the optimized echo signal evolution curve.

The second unit (e.g. echo signal evolution curve calculator) 442 obtains a calculated echo signal evolution curve by means of calculation according to the optimized variable flip angles.

The third unit (e.g. comparator) 443 compares the calculated echo signal evolution curve with the optimized echo signal evolution curve and uses, when a difference between the two satisfies a specified requirement, the optimized variable flip angles as the actual variable flip angle train.

FIGS. 5A to 5D show a comparison diagram of a group of brain images acquired when imaging is performed using a traditional BLADE sequence and using a BLADE sequence with a flip angle according to exemplary embodiments of the present disclosure.

Figure 5A:
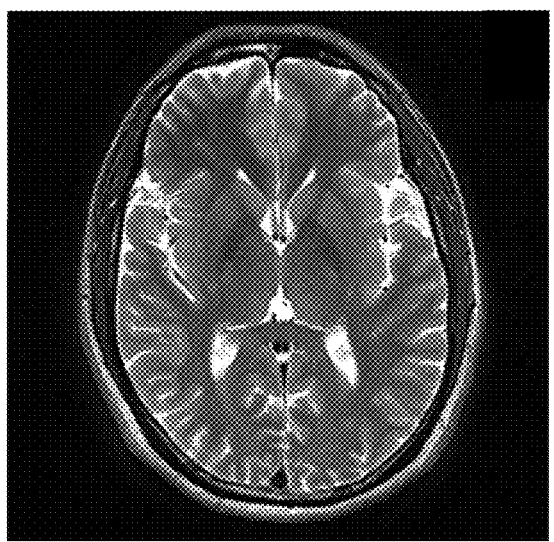
FIGS. 5A to 5D illustrate a comparison diagram of a group of brain images acquired when imaging is performed using a traditional BLADE sequence and using a BLADE sequence with a flip angle according to an exemplary embodiment of the present disclosure.
Figure 5B:
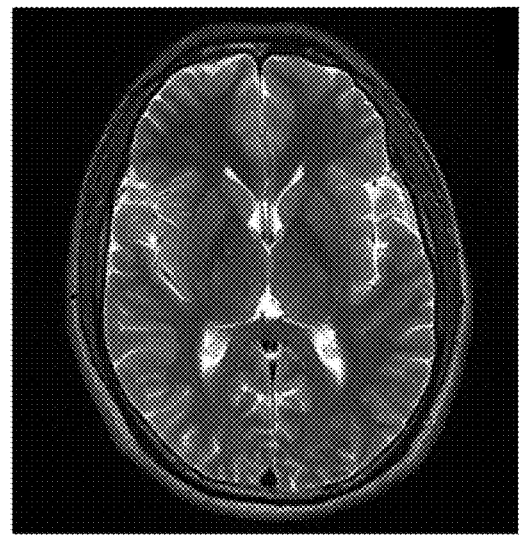

FIG. 5A is an axial image of the brain that is acquired when imaging is performed using a traditional BLADE sequence, and FIG. 5B is an axial image of the brain that is acquired when imaging is performed using a BLADE sequence with a flip angle in the embodiments of the present disclosure. It may be seen that the image contrast and the image quality of the image shown in FIG. 5B are equivalent to the image contrast and the image quality of the image shown in FIG. 5A, but a scanning speed is increased by 52% since a blade width is increased.

Figure 5C:
Figure 5D:
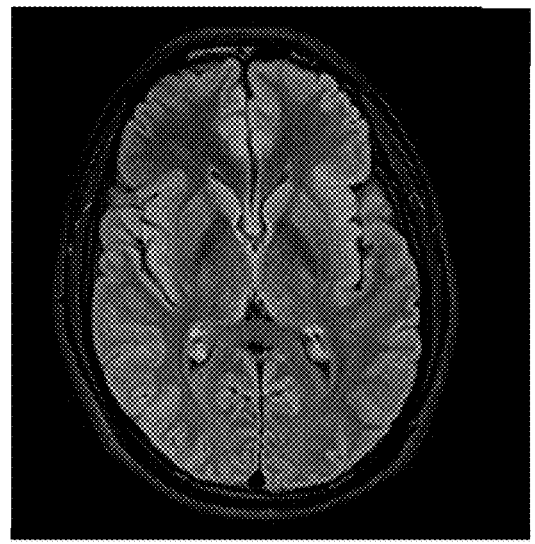

FIG. 5C is an axial image of the brain that is acquired when imaging is performed using a traditional BLADE fluid attenuated inversion recovery sequence, and FIG. 5D is an axial image of the brain that is acquired when imaging is performed using a BLADE fluid attenuated inversion recovery sequence with a flip angle in the embodiments of the present disclosure. It may be seen that the image contrast and the image quality of the image shown in FIG. 5D are equivalent to the image contrast and the image quality of the image shown in FIG. 5C, but a scanning speed is increased by 61% since a blade width is increased.

FIGS. 6A to 6D show a comparison diagram of a group of knee images acquired when imaging is performed using a traditional BLADE sequence and using a BLADE sequence with a flip angle according to exemplary embodiments of the present disclosure.

Figure 6A:
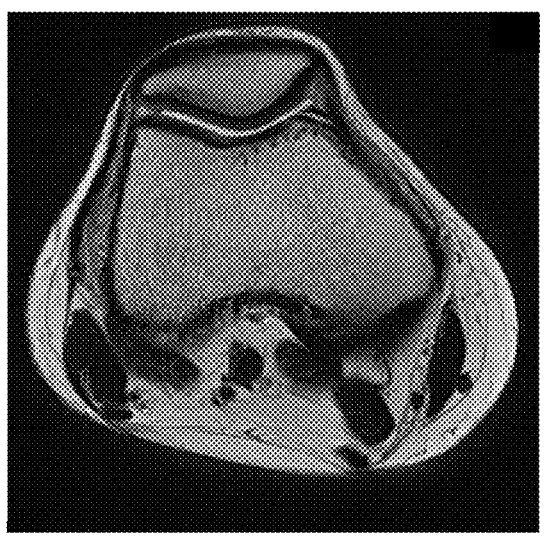
FIGS. 6A to 6D illustrate a comparison diagram of a group of knee images acquired when imaging is performed using a traditional BLADE sequence and using a BLADE sequence with a flip angle according to an exemplary embodiment of the present disclosure.
Figure 6B:

FIG. 6A is an axial image of the knee that is acquired when imaging is performed using a traditional BLADE sequence, and FIG. 6B is an axial image of the knee that is acquired when imaging is performed using a BLADE sequence with a flip angle in the embodiments of the present disclosure. It may be seen that the image contrast and the image quality of the image shown in FIG. 6B are equivalent to the image contrast and the image quality of the image shown in FIG. 6A, but a scanning speed is increased by 42% since a blade width is increased.

Figure 6C:
Figure 6D:
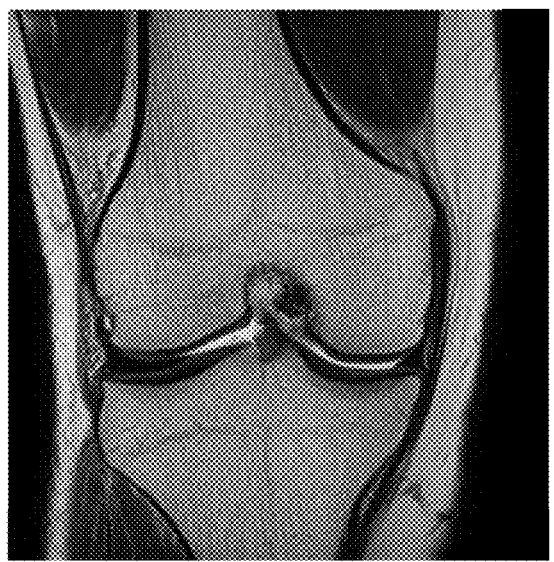

FIG. 6C is a coronal plane image of the knee that is acquired when imaging is performed using a traditional BLADE sequence, and FIG. 6D is a coronal plane image of the knee that is acquired when imaging is performed using a BLADE sequence with a flip angle in the embodiments of the present disclosure. It may be seen that the image contrast and the image quality of the image shown in FIG. 6D are equivalent to the image contrast and the image quality of the image shown in FIG. 6C, but a scanning speed is increased by 45% since a blade width is increased.

Figure 7A:
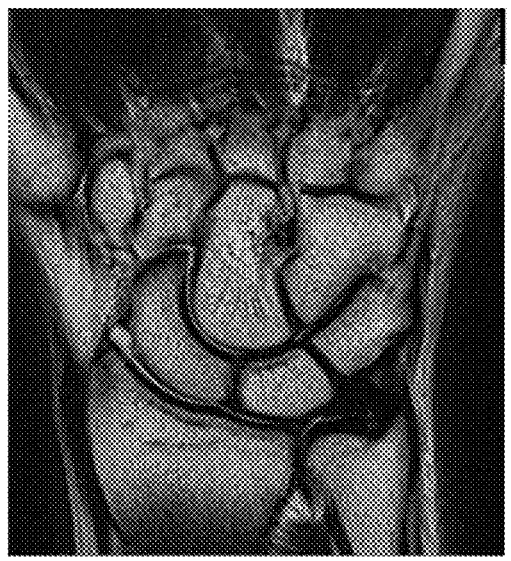
FIGS. 7A and 7B illustrate a comparison diagram of a group of wrist images acquired when imaging is performed using a traditional BLADE sequence and using a BLADE sequence with a flip angle according to an exemplary embodiment of the present disclosure.
Figure 7B:

FIGS. 7A and 7B show a comparison diagram of a group of wrist images acquired when imaging is performed using a traditional BLADE sequence and using a BLADE sequence with a flip angle according to exemplary embodiments of the present disclosure.

FIG. 7A is a coronal plane image of the wrist that is acquired when imaging is performed using a traditional BLADE sequence, and FIG. 7B is a coronal plane image of the wrist that is acquired when imaging is performed using a BLADE sequence with a flip angle in the embodiments of the present disclosure. It may be seen that the image contrast and the image quality of the image shown in FIG. 7B are equivalent to the image contrast and the image quality of the image shown in FIG. 7A, but a scanning speed is increased by 39% since a blade width is increased.

It can be seen from the solutions described above that in the embodiments of the present disclosure, an optimized echo signal evolution curve is first determined; based on the echo signal evolution curve, a magnetic resonance image can satisfy a preset contrast, and the acquisition time of a BLADE sequence can satisfy a specified short-time requirement; a variable flip angle train is then obtained by means of calculation based on the optimized echo signal evolution curve; and the variable flip angle train is applied to a two-dimensional fast spin echo sequence, and a blade artifact correction sequence corresponding to the second adjustment parameter is used to acquire magnetic resonance signals. Therefore, attenuation of T2 can be controlled by adjusting a value of a flip angle when a blade width is increased, and then, on the premise of ensuring the imaging quality and the contrast of an image, a scanning time can be reduced by increasing the blade width and more common data in the center of k-space can be further obtained, which can better perform motion correction and reduce artifacts.

Further, an imaging parameter for a variable flip angle mode is set, so that an image satisfying a desired tissue contrast may be implemented by adjusting the imaging parameter.

Furthermore, the embodiments of the present disclosure provide a simple and reliable implementation of an optimized variable flip angle train.

The above description is only preferred embodiments of the present disclosure and is not intended to limit the present disclosure, and any modifications, equivalent replacements, improvements, etc. made within the spirit and principles of the present disclosure should be included within the scope of protection of the present disclosure.

References in the specification to "one embodiment," "an embodiment," "an exemplary embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

The exemplary embodiments described herein are provided for illustrative purposes, and are not limiting. Other exemplary embodiments are possible, and modifications may be made to the exemplary embodiments. Therefore, the specification is not meant to limit the disclosure. Rather, the scope of the disclosure is defined only in accordance with the following claims and their equivalents.

Embodiments may be implemented in hardware (e.g., circuits), firmware, software, or any combination thereof. Embodiments may also be implemented as instructions stored on a machine-readable medium, which may be read and executed by one or more processors. A machine-readable medium may include any mechanism for storing or transmitting information in a form readable by a machine (e.g., a computer). For example, a machine-readable medium may include read only memory (ROM); random access memory (RAM); magnetic disk storage media; optical storage media; flash memory devices; electrical, optical, acoustical or other forms of propagated signals (e.g., carrier waves, infrared signals, digital signals, etc.), and others. Further, firmware, software, routines, instructions may be described herein as performing certain actions. However, it should be appreciated that such descriptions are merely for convenience and that such actions in fact results from computing devices, processors, controllers, or other devices executing the firmware, software, routines, instructions, etc. Further, any of the implementation variations may be carried out by a general purpose computer.

For the purposes of this discussion, the term "processor circuitry" shall be understood to be circuit(s), processor(s), logic, or a combination thereof. A circuit includes an analog circuit, a digital circuit, state machine logic, data processing circuit, other structural electronic hardware, or a combination thereof. A processor includes a microprocessor, a digital signal processor (DSP), central processor (CPU), application-specific instruction set processor (ASIP), graphics and/or image processor, multi-core processor, or other hardware processor. The processor may be "hard-coded" with instructions to perform corresponding function(s) according to aspects described herein. Alternatively, the processor may access an internal and/or external memory to retrieve instructions stored in the memory, which when executed by the processor, perform the corresponding function(s) associated with the processor, and/or one or more functions and/or operations related to the operation of a component having the processor included therein.

In one or more of the exemplary embodiments described herein, the memory is any well-known volatile and/or non-volatile memory, including, for example, read-only memory (ROM), random access memory (RAM), flash memory, a magnetic storage media, an optical disc, erasable programmable read only memory (EPROM), and programmable read only memory (PROM). The memory can be non-removable, removable, or a combination of both.

REFERENCE LIST

L Blade width
201-205 Steps
410 First adjustment parameter determiner
420 Second adjustment parameter determiner
430 Echo signal evolution curve determiner
440 Variable flip angle train determiner
441 First unit
442 Second unit
443 Third unit
450 Magnetic resonance imaging scanner

The invention claimed is:

1. A magnetic resonance imaging method based on a two-dimensional fast spin echo sequence, which uses a Balanced Steady State Free Precession Line Acquisition with Undersampling (BLADE) artifact correction sequence to perform data acquisition of magnetic resonance signals, the method comprising:
  determining a first adjustment parameter to preset an initial contrast of a magnetic resonance image;
  after the determining the first adjustment parameter to preset the initial contrast of the magnetic resonance image, (i) calculating an initial predetermined echo signal evolution curve based on the first adjustment parameter, and (ii) calculating an initial variable flip angle train based on the initial predetermined echo signal evolution curve;
  determining a second adjustment parameter to obtain an optimized contrast of the magnetic resonance image and a specified data acquisition time of the BLADE artifact correction sequence;
  determining an optimized echo signal evolution curve based on the first adjustment parameter and the second adjustment parameter;

calculating an actual variable flip angle train based on the optimized echo signal evolution curve; and applying the actual variable flip angle train to the two-dimensional fast spin echo sequence, and using the BLADE artifact correction sequence corresponding to the second adjustment parameter to acquire magnetic resonance signals and enable the magnetic resonance image to satisfy the optimized contrast.

2. The magnetic resonance imaging method according to claim 1, wherein the second adjustment parameter comprises an echo spacing and/or an echo train length.

3. The magnetic resonance imaging method according to claim 1, wherein the calculating the actual variable flip angle train comprises:

reckoning optimized variable flip angles based on the optimized echo signal evolution curve;

calculating a calculated echo signal evolution curve based on the optimized variable flip angles; and comparing the calculated echo signal evolution curve with the optimized echo signal evolution curve and selectively using, based on a result of the comparison satisfying a predetermined criterion, the optimized variable flip angles as the actual variable flip angle train.

4. The magnetic resonance imaging method according to claim 3, wherein the optimized variable flip angles are used as the actual variable flip angle train when a difference between the calculated echo signal evolution curve and the optimized echo signal evolution curve satisfies a specified requirement in accordance with the predetermined criterion.

5. The magnetic resonance imaging method based on two-dimensional fast spin echo according to claim 1, wherein the first adjustment parameter comprises one of the following preset variable flip angle modes:

longitudinal magnetization vector relaxation time T1-weighted, proton density PD-weighted, or transverse magnetization vector relaxation time T2-weighted.

6. A non-transitory computer-readable storage medium with an executable program stored thereon, that when executed, instructs a processor to perform the method of claim 1.

7. A non-transitory computer program product having a computer program which is directly loadable into a memory of a controller of a magnetic resonance device that, when executed by the controller, causes the magnetic resonance device to perform the method as claimed in claim 1.

8. The magnetic resonance imaging method according to claim 1, wherein determining the second adjustment parameter comprises determining an increased echo train length that increases a BLADE width to thereby reduce a data acquisition time of the BLADE artifact correction sequence.

9. The magnetic resonance imaging method according to claim 8, wherein the reduction in data acquisition time of the BLADE artifact correction sequence enables the magnetic resonance image to satisfy the optimized contrast so as to eliminate artifacts.

10. The magnetic resonance imaging method according to claim 1, wherein the first adjustment parameter comprises one of a longitudinal magnetization vector relaxation time T1-weighted preset variable flip angle mode, a proton density PD-weighted preset variable flip angle mode, or a transverse magnetization vector relaxation time T2-weighted preset variable flip angle mode, and wherein the second adjustment parameter comprises an echo spacing and/or an echo train length.

11. The magnetic resonance imaging method according to claim 1, wherein the calculating the actual variable flip angle train comprises:

calculating the actual variable flip angle based on the optimized echo signal evolution curve by selecting from among (i) an initial variable flip angle train that is calculated based upon a predetermined echo signal evolution curve that is based on the first adjustment parameter, or (ii) an optimized flip angle train that is calculated based on the optimized echo signal evolution curve.

12. The magnetic resonance imaging method according to claim 1, wherein the actual variable flip angle train comprises variable flip angles introduced into the BLADE artifact correction sequence to control attenuation of transverse magnetization vector relaxation time T2 by adjusting a value of the flip angle as BLADE width is increased.

13. The magnetic resonance imaging method according to claim 12, wherein the variable flip angles of the actual variable flip angle train increase an echo train length while reducing an effect of attenuation of the transverse magnetization vector relaxation time T2.

14. A magnetic resonance imaging apparatus using a two-dimensional fast spin echo sequence, which uses a Balanced Steady State Free Precession Line Acquisition with Undersampling (BLADE) artifact correction sequence to perform data acquisition of magnetic resonance signal, the apparatus comprising:

a first adjustment parameter determiner configured to determine a first adjustment parameter to preset an initial contrast of a magnetic resonance image;

a second adjustment parameter determiner configured to determine a second adjustment parameter to obtain an optimized contrast of the magnetic resonance image and a specified data acquisition time of the BLADE artifact correction sequence;

an echo signal evolution curve determiner configured to calculate an initial predetermined echo signal evolution curve based on the first adjustment parameter, and to determine an optimized echo signal evolution curve based on the first adjustment parameter and the second adjustment parameter;

a variable flip angle train determiner configured to calculate an initial variable flip angle train based on the initial predetermined echo signal evolution curve, and to calculate an actual variable flip angle train based on to the optimized echo signal evolution curve; and a magnetic resonance imaging scanner configured to:

apply the actual variable flip angle to the two-dimensional fast spin echo sequence; and use the BLADE artifact correction sequence corresponding to the second adjustment parameter to acquire magnetic resonance signals and enable the magnetic resonance image to satisfy the optimized contrast.

15. The magnetic resonance imaging apparatus according to claim 14, wherein the second adjustment parameter determiner determines an echo spacing and/or an echo train length for obtaining the optimized contrast of the magnetic resonance image, and an echo train length for obtaining the specified data acquisition time of the BLADE artifact correction sequence.

16. The magnetic resonance imaging apparatus according to claim 14, wherein the variable flip angle train determiner comprises:

a reckoner configured to obtain optimized variable flip angles based on the optimized echo signal evolution curve;

an echo signal evolution curve calculator configured to calculate a calculated echo signal evolution curve based on the optimized variable flip angles; and a comparator configured to compare the calculated echo signal evolution curve with the optimized echo signal evolution curve and selectively use, based on a result of the comparison satisfying a predetermined criterion, the optimized variable flip angles as the actual variable flip angle train.

17. The magnetic resonance imaging apparatus according to claim 16, wherein the optimized variable flip angles are used as the actual variable flip angle train when a difference between the calculated echo signal evolution curve and the optimized echo signal evolution curve satisfies a specified requirement in accordance with the predetermined criterion.

18. The magnetic resonance imaging apparatus according to claim 14, wherein the first adjustment parameter determiner is configured to determine a variable flip angle mode for presetting the initial contrast of the magnetic resonance image, the variable flip angle mode being one of the following variable flip angle modes:

longitudinal magnetization vector relaxation time T1-weighted, proton density PD-weighted, or transverse magnetization vector relaxation time T2-weighted.

19. A magnetic resonance imaging apparatus based on a two-dimensional fast spin echo sequence, which uses a Balanced Steady State Free Precession Line Acquisition with Undersampling (BLADE) artifact correction sequence to perform data acquisition of magnetic resonance signal, the apparatus comprising:

a processor that is configured to:
    determine a first adjustment parameter to preset an initial contrast of a magnetic resonance image;
    after the first adjustment parameter to preset the initial contrast of the magnetic resonance image, (i) calculate an initial predetermined echo signal evolution curve based on the first adjustment parameter, and (ii) calculate an initial variable flip angle train based on the initial predetermined echo signal evolution curve;
    determine a second adjustment parameter to obtain an optimized contrast of the magnetic resonance image and a specified data acquisition time of the BLADE blade-artifact correction sequence;
    determine an optimized echo signal evolution curve based on the first adjustment parameter and the second adjustment parameter; and
    calculate an actual variable flip angle train based on to the optimized echo signal evolution curve; and a magnetic resonance imaging scanner configured to:
    apply the actual variable flip angle to the two-dimensional fast spin echo sequence; and
    use the BLADE artifact correction sequence corresponding to the second adjustment parameter to acquire magnetic resonance signals and enable the magnetic resonance image to satisfy the optimized contrast.

* * * * *